(12) United States Patent
Kim et al.

(10) Patent No.: US 9,996,918 B2
(45) Date of Patent: Jun. 12, 2018

(54) METHOD FOR DISTINGUISHING PULMONARY ARTERY AND PULMONARY VEIN, AND METHOD FOR QUANTIFYING BLOOD VESSELS USING SAME

(71) Applicant: The Asan Foundation, Seoul (KR)

(72) Inventors: Nam Kug Kim, Seoul (KR); Joon Beom Seo, Seoul (KR); Se Youn Park, Seoul (KR); Sang Min Lee, Seoul (KR)

(73) Assignee: The Asan Foundation, Seoul (KR)

( * ) Notice: Subject to any disclaimer, the term of this patent is extended or adjusted under 35 U.S.C. 154(b) by 0 days. days.

(21) Appl. No.: 14/881,817

(22) Filed: Oct. 13, 2015

(65) Prior Publication Data
US 2016/0117814 A1   Apr. 28, 2016

Related U.S. Application Data

(63) Continuation of application No. PCT/KR2014/002244, filed on Mar. 17, 2014.

(30) Foreign Application Priority Data

Apr. 10, 2013 (KR) .................. 10-2013-0039075
Aug. 19, 2013 (KR) .................. 10-2013-0097769

(51) Int. Cl.
  *G06T 7/00* (2017.01)
  *A61B 6/00* (2006.01)
  (Continued)

(52) U.S. Cl.
  CPC ............ *G06T 7/0012* (2013.01); *A61B 6/032* (2013.01); *A61B 6/504* (2013.01); *A61B 6/5217* (2013.01);
  (Continued)

(58) Field of Classification Search
  USPC .......................................... 382/128
  See application file for complete search history.

(56) References Cited

U.S. PATENT DOCUMENTS 5,971,767 A   10/1999   Kaufman et al.
6,331,116 B1  12/2001   Kaufman et al.
(Continued)

FOREIGN PATENT DOCUMENTS

JP   2009-525072 A   7/2009
JP   2010-220742 A   10/2010
(Continued)

*Primary Examiner* — Ishrat I Sherali
(74) *Attorney, Agent, or Firm* — Mintz Levin Cohn Ferris Glovsky and Popeo, P.C.; Kongsik Kim; Katherine C. Jensen

(57) ABSTRACT

A method for distinguishing between pulmonary arteries and pulmonary veins and a method for quantifying blood vessels are disclosed. The method for distinguishing between pulmonary arteries and pulmonary veins includes: forming a set of pulmonary vessels for points corresponding to pulmonary vessels, wherein each of the points of the set of pulmonary vessels has weight information; forming a tree from the points of the set of pulmonary vessels by using the weight information; and distinguishing between the pulmonary arteries and the pulmonary veins by separating the tree into a plurality of regions. The method for quantifying blood vessels includes: extracting blood vessels as a three-dimensional set of voxels based on medical images of an organ; finding the voxels of blood vessels included in a region of interest of the organ; and quantifying length information of the blood vessels by using the found voxels.

14 Claims, 21 Drawing Sheets

(51) Int. Cl.
  *A61B 6/03*  (2006.01)
  *G06K 9/46*  (2006.01)
  *G06K 9/52*  (2006.01)
  *G06K 9/62*  (2006.01)

(52) U.S. Cl.
  CPC ............ *G06K 9/4604* (2013.01); *G06K 9/52* (2013.01); *G06K 9/6267* (2013.01); *G06K 2009/4666* (2013.01); *G06T 2200/04* (2013.01); *G06T 2207/30061* (2013.01); *G06T 2207/30101* (2013.01)

(56) References Cited

U.S. PATENT DOCUMENTS

| | | | |
|---|---|---|---|
| 6,343,936 B1 | 2/2002 | Kaufman et al. | |
| 7,356,367 B2* | 4/2008 | Liang | A61B 5/055 600/407 |
| 7,477,768 B2* | 1/2009 | Kaufman | G06T 7/0012 378/41 |
| 7,486,811 B2* | 2/2009 | Kaufman | G06T 7/0012 378/21 |
| 7,876,936 B2 | 1/2011 | Raffy | |
| 7,970,189 B2 | 6/2011 | Buelow et al. | |
| 8,019,140 B2 | 9/2011 | Odry et al. | |
| 8,447,081 B2 | 5/2013 | Lakare et al. | |
| 8,526,690 B2 | 9/2013 | Kitamura | |
| 8,605,978 B2* | 12/2013 | Mizuno | G06T 7/0012 382/128 |
| 8,761,473 B2 | 6/2014 | Ihara | |
| 8,818,061 B2* | 8/2014 | Ohlson | G06T 7/0083 382/128 |
| 8,913,060 B2* | 12/2014 | Kassab | G06T 7/0012 345/424 |
| 9,483,832 B2* | 11/2016 | Itai | G06T 7/0081 |
| 2001/0031920 A1* | 10/2001 | Kaufman | A61B 5/055 600/431 |
| 2007/0276255 A1* | 11/2007 | Leban | A61B 17/22012 600/471 |
| 2012/0207364 A1* | 8/2012 | Ohlson | G06T 7/0083 382/128 |
| 2012/0269410 A1 | 10/2012 | Ihara | |

FOREIGN PATENT DOCUMENTS

| | | |
|---|---|---|
| JP | 2012-223338 A | 11/2012 |
| KR | 10-1144774 B1 | 5/2012 |
| KR | 10-1189739 B1 | 10/2012 |
| KR | 10-1441089 B1 | 9/2014 |

* cited by examiner

Overall procedure for vessel classification

Result of pulmonary vessel segmentation and classification (a) The initial tree (b) Medial line extraction (a) Nearest boundary points  (b) Cylinder fitting and radius calculation Radius calculation (a) Gradual peeling by 5mm intervals from the outermost pulmonary surface (b) Vascular (c) Texture mapping (d) Surfel computation (a) Distance field generation using an octree (b)Initial boundary surface (left) and inner surface extraction (right)

Inner surface and vessel intersection extraction (a) (b) (c) (d) (e)

Region extraction by the mono-oriented region partition method (a) Lung extraction(left) and distance field generation (right)

(b) Cavity region extraction (c) Coronal view of the mediastinal region extraction result (a) an intersection between an inner offset surface and pulmonary vessels (b) vascular orientation estimation (a) 3D rendering of the intersecting vessels as disks (b) surfels only, arteries and veins from left to right, respectively Accuracy test for the radius estimation with virtual vascular phantom models (a) The number of vessels by gradual peeling (b) Mean diameter(mm) by gradual peeling (c) The occupied area percentage of the vessels by gradual peeling (d) Mean diameter(mm) using tree branching levels

METHOD FOR DISTINGUISHING PULMONARY ARTERY AND PULMONARY VEIN, AND METHOD FOR QUANTIFYING BLOOD VESSELS USING SAME

CROSS-REFERENCE TO RELATED APPLICATION

This application is a continuation of PCT/KR2014/002244 filed on Mar. 17, 2014, which claims priority to Korean Application Nos. 10-2013-0039075 and 10-2013-0097769 filed on Apr. 10, 2013 and Aug. 19, 2013, respectively, which applications are incorporated herein by reference.

TECHNICAL FIELD

The present disclosure relates generally to a method for distinguishing between pulmonary arteries and pulmonary veins, and a method for quantifying blood vessels by using the same, and more particularly to a method for distinguishing between pulmonary arteries and pulmonary veins using a minimum spanning tree, and a method for quantifying the diameters of blood vessels and thus quantifying the distributions and scales of the blood vessels in an organ by using the same.

BACKGROUND ART

This section provides background information related to the present disclosure which is not necessarily prior art.

The state of blood vessels can be used as an index for diseases of an organ. For example, the state of pulmonary vessels has emerged as an meaningful index for many lung diseases, such as pulmonary hypertension, interstitial lung disease and chronic obstructive pulmonary disease (COPD) (see the paper by M. G. Linguraru et al., "Segmentation and quantification of pulmonary artery for noninvasive CT assessment of sickle cell secondary pulmonary hypertension," Medical Physics, vol. 37(4), pp. 1522-1532, 2010).

The state of pulmonary vessels, particularly the result of the analysis of the distribution and scale of small pulmonary vessels, is one of the meaningful evaluation indices for the state of a pulmonary circulation state, and is essential for the analysis of various lung diseases.

Recent research shows that there are relationships between the measurable morphological characteristics of pulmonary vessels, such as diameters and an area percentage estimated from computerized tomography (CT) images, and various clinical parameters.

Various researches suggest that there is a close relationship between endothelial dysfunction, asserted to be related to pulmonary emphysema, and vascular alteration (see the paper by Santos et al., "Enhanced expression of vascular endothelial growth factor in pulmonary arteries of smokers and patients with moderate chronic obstructive pulmonary disease," American Journal of Respiratory and Critical Care Medicine, vol. 167, pp. 1250-1256, 2003).

From the technological point of view, an attempt has been made to measure the morphological characteristics of large blood vessels using vascular contrast enhanced images (see the paper by Barrier et al., "Today's and tomorrow's imaging and circulating biomarkers for pulmonary arterial hypertension," Cellular and Molecular Life Sciences, vol. 69, pp. 2805-2831, 2012).

However, there has rarely been an attempt to evaluate the morphological characteristics of small vessels.

Meanwhile, an attempt was made to perform simple thresholding in a two-dimensional (2D) sectional CT image in order to quantify pulmonary vessels, select circular regions having an area smaller than 5 mm$^2$ as blood vessels, and show a correlation between the small areas of pulmonary vessels and a pulmonary function test (PFT) (see the paper by Matsuoka et al., "Quantitative computed tomographic measurement of a cross-sectional area of a small pulmonary vessel in nonsmokers without airflow limitation," Japanese Journal of Radiology, vol. 29, pp. 251-255, 2011).

However, although the paper (by Matsuoka et al.) shows a strong clinical relationship between the distribution of blood vessels and a PFT, a pulmonary artery and a pulmonary vein are not distinguished from each other, it is difficult to accurately measure the diameter of a blood vessel in a direction orthogonal to the axis of the blood vessel because 2D slice images are used, and it is difficult to assert that the results of the research were obtained by an accurate quantification of the overall three-dimensional (3D) lungs.

The development of medical image technology, particularly the development of 3D CT images, enables small sub-millimeter structures to be observed in a living body. There has been rapid advancement not only in spatial resolution but also in temporal resolution. However, it is difficult to quantify small blood vessels based on 3D CT images via an automated algorithm due to the complicated morphological structures of blood vessels, for example, a densely populated distribution, proximately intersecting cases, other parallel neighbor blood vessels, etc. In particular, there has not been a successful attempt to classify small blood vessels into arteries and veins and then quantify them based on 3D CT images via an automated algorithm.

It is not easy to segment and/or classify pulmonary arteries and pulmonary veins. Since pulmonary vessels are densely distributed across the lungs and the morphological characteristics (radii, branching patterns, etc.) thereof vary from person to person, it is not easy to distinguish the blood vessels even when the pulmonary vessels have been segmented. Furthermore, since pulmonary arteries and pulmonary veins intersect each other, they are seen as overlapping each other in a 3D image, such as a CT image. Related technology includes a technology disclosed in the paper by T. Buelow, R. Wiemker, T. Blaffert, C. Lorenz, S. Renisch, "Automatic extraction of the pulmonary artery tree from multi-slice CT data," Medical Imaging 2005: Physiology, Function, and Structure from Medical Images. Proceedings of the SPIE, 5746, pp. 730-740, Apr. 2005."

Therefore, there is a need for developing a method for distinguishing between pulmonary arteries and veins via an automated algorithm, three-dimensional visualization of arteries and vein in an organ and quantifying the blood vessels, including diameters and lengths, throughout the organ based on the state of the blood vessels.

SUMMARY OF THE DISCLOSURE

This section provides a general summary of the disclosure and is not a comprehensive disclosure of its full scope or all of its features.

According to one aspect of the present disclosure, there is provided a method for distinguishing between pulmonary arteries and pulmonary veins, including: forming a set of pulmonary vessels for points corresponding to pulmonary vessels including pulmonary arteries and pulmonary veins, wherein each of the points of the set of pulmonary vessels has weight information including an intensity weight and a local shape weight; forming a tree from the points of the set of pulmonary vessels by using the weight information; and distinguishing between the pulmonary arteries and the pulmonary veins by separating the tree into a plurality of regions.

According to another aspect of the present disclosure, there is provided a method for quantifying blood vessels, including: extracting blood vessels as a three-dimensional (3D) set of voxels based on medical images of an organ; finding the voxels of blood vessels included in a region of interest of the organ; and quantifying length information of the blood vessels, including diameters of the blood vessels, by using the found voxels.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

The present disclosure will now be described in detail with reference to the accompanying drawings.

1. Vessel Segmentation

Figure 1:
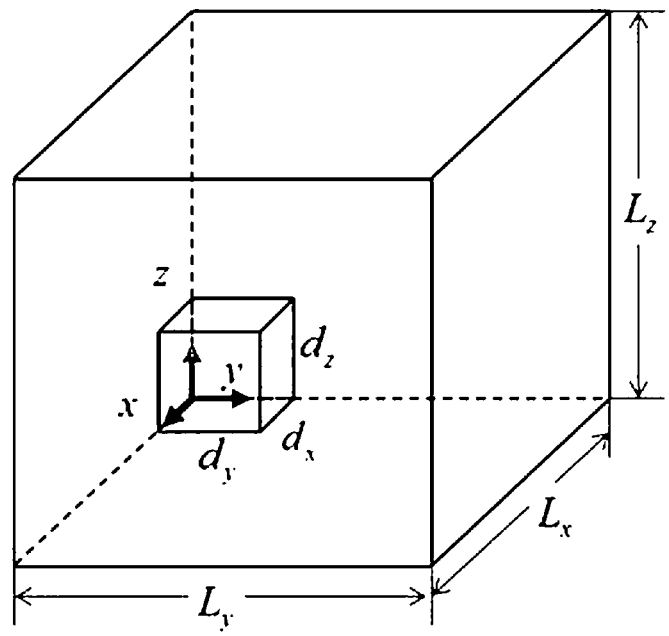
FIG. 1 is a diagram illustrating the structure of volume data.

In the present disclosure, as a preprocessing process prior to segmentation, voxels corresponding to blood vessels are extracted from medical images (for example, computerized tomography (CT) images). For this purpose, two closed regions corresponding to the lungs are extracted. As shown in FIG. 1, 3D volume data for which the present disclosure is targeted is composed of uniform Voxel $n=(n_x, n_y, n_z)^T$ voxels having a size of $d=(d_x, d_y, d_z)^T$, and has a range of $L=d \cdot n=(L_x, L_y, L_z)^T$. Prior to a detailed description of an algorithm, the structural morphology of the lungs is described in order to use the known anatomy of pulmonary vessels as prior knowledge.

1. A. Pulmonary Vessel Anatomy

Figure 2:
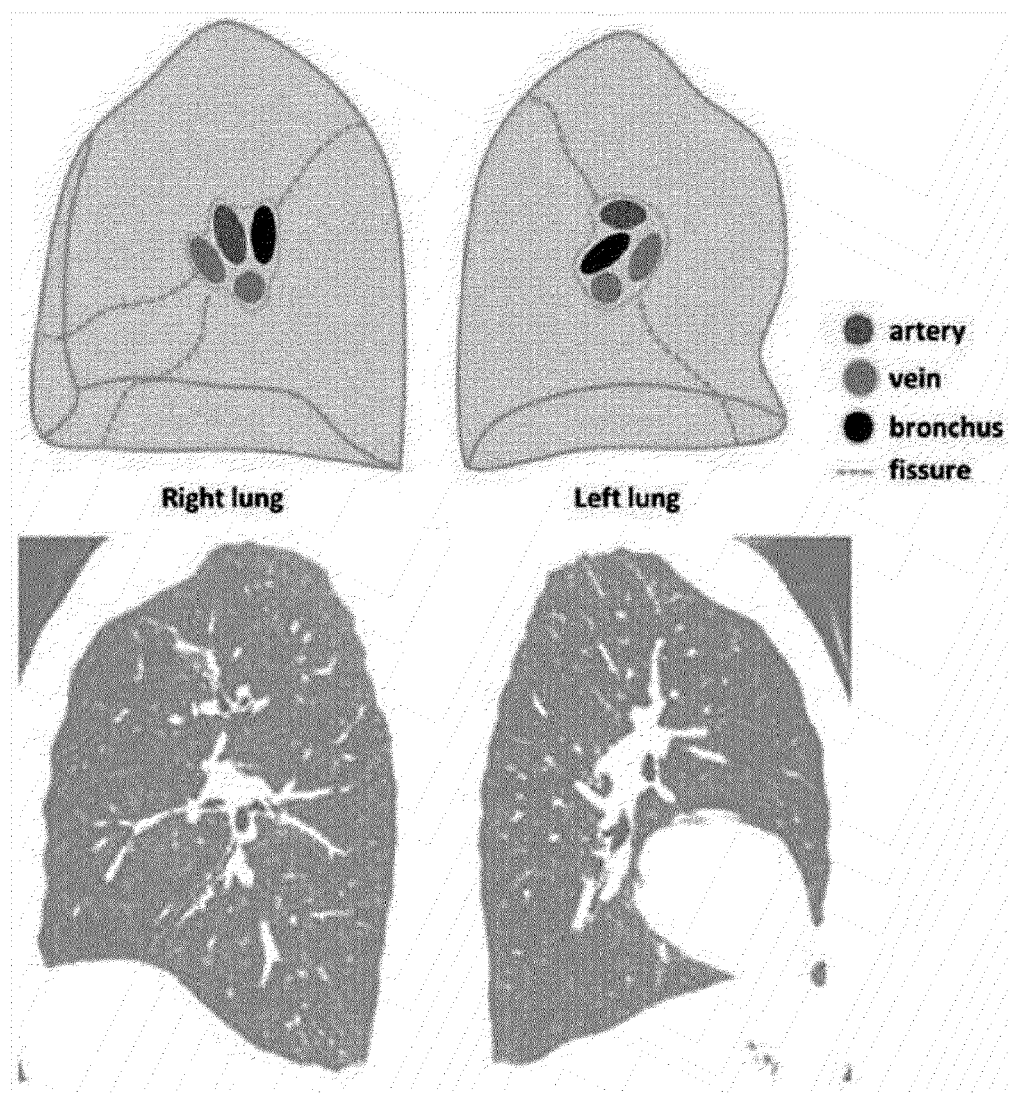
FIG. 2 shows views illustrating the schematic shapes of the left and right lungs when viewed from a mediastinal view.

FIG. 2 shows the schematic shapes of the left and right lungs when viewed from a mediastinal view. Generally, when a section is viewed from the mediastinal view, the bronchus, a pulmonary artery, and two pulmonary veins are located in the central portion of each of the left and right lungs. Since the bronchus, the pulmonary artery, and the pulmonary veins are generally close to one another and only attenuation density is determined in a CT image, the pulmonary artery and the pulmonary veins are not distinguished from each other and are seen as a single region. Furthermore, since the wall of the bronchus, the blood vessels, a fissure, etc. have similar intensities inside the lungs in a non-contrast enhanced image, it is difficult to perform simple classification using only intensities.

1. B. Pulmonary Vessel Extraction

Figure 3:
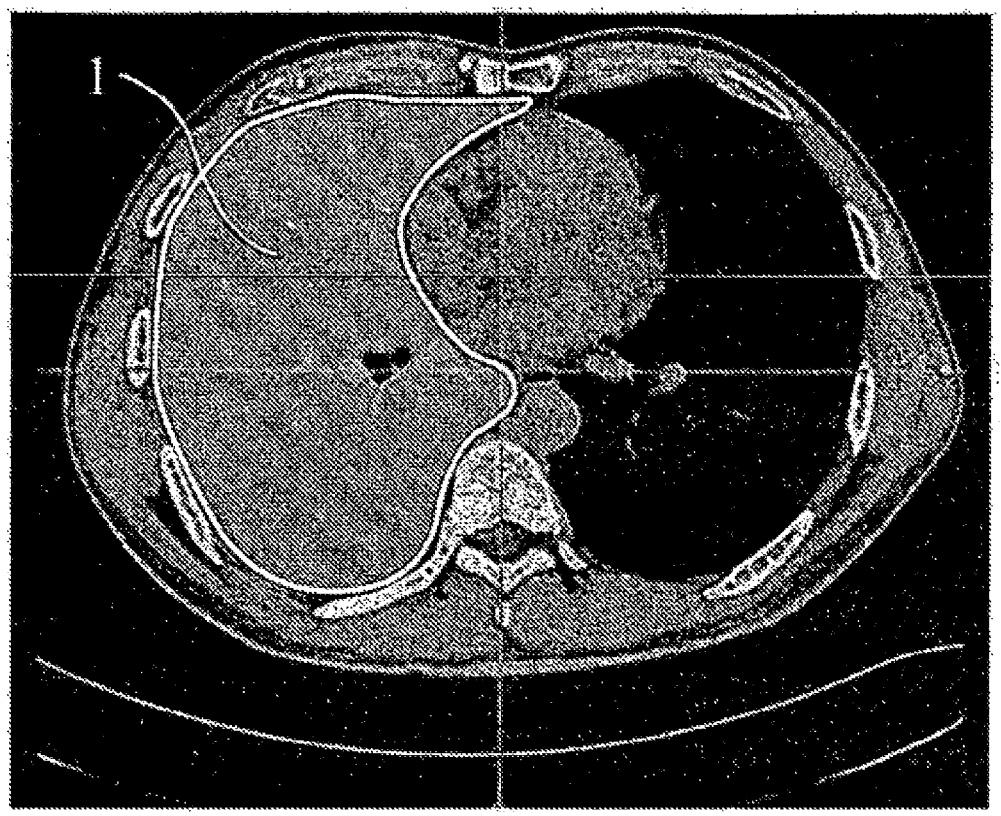
FIG. 3 is a view illustrating an example of a pulmonary CT image.

An input 3D volume CT image is set to a set of voxels, i.e., $V=\{c|c=(i,j,k), i=1, \ldots, n_x, j=1, \ldots, n_y, k=1, \ldots, n_z\}$. Furthermore, the intensity value in a cell c is set to I(c). Voxels corresponding to the two lungs (excluding the bronchus and the wall of the bronchus) are extracted, as in the green regions of FIG. 3, and then, for example, cells having a value equal to or greater than −600 HU among the inner voxels are extracted as a set of initial pulmonary vessels. In this case, a conservative reference value is used to exclude points other than vessels as much as possible.

After the initial blood vessel candidate cells have been extracted, small blood vessels having low intensity in pulmonary peripheral portions are extracted via modified region growing (see [14]). In this case, a tissue, such as a fissure, other than a vessel, may be also extracted. In order to process this in a later process, the intensity value of each cell is stored. ([14]: Y. Sato, S. Nakajima, N. Shiraga, H. Atsumi, S. Yoshida, T. Koller, G. Gerig, R. Kikins, "Three-dimensional multi-scale line filter for segmentation and visualization of curvilinear structures in medical images," Medical Image Analysis, vol. 2, no. 2, pp. 143-168, 1998).

A set of cells (a set of pulmonary vessels) extracted as described above is set to $Pv=\{v(c)\}$. In this case, $v(c)$ is a vector composed of the center coordinate of a cell c and a weight, and may be defined as follows. $v=(x, y, z, w)^T = (v_p^T, w)^T$, where $V_p=(x, y, z)^T=((c_i-0.5)d_x, (c_j-0.5)d_y, (c_k-0.5)d_z)^T$. The weight w is calculated using $w=w_1 \times w_2$, where $w_1$ is a weight calculated from an intensity defined as $w_1=(i-i_{min})/(i_{max}-i_{min})$. In this case, $i_{max}=\max\{I(v_i)\}$ and $i_{min}=\min\{I(v_i)\}$. $w_2$ is a weight representative of a local shape (a local shape weight), which will be described later.

When blood vessels are extracted using only intensities, it is difficult to distinguish between a tissue having a similar intensity, such as a fissure, and a micro-vessel. Accordingly, in this disclosure, a weight representative of a local shape is defined, and then whether an object in question is a vessel is additionally determined via each point and its peripheral shape. First, in order to eliminate a fissure, the eigenvalue $\lambda$ of difference vector $\{(q_p-v_{pi})|q_p \in N(v_i)\}$ is calculated using a set $N(v_i)$ of cells having a value equal to or greater than −750 HU among 30 neighbor cells at each point $v_i$ as a local shape index, and then $\lambda_{min}/\lambda_{max}$ is calculated using a minimum value $\lambda_{min}$ and a maximum value $\lambda_{max}$. As this value decreases, a shape in question becomes more similar to a plane. Points having a value equal to or less than a predetermined value of 0.15 are determined to correspond to a fissure, and are assigned $w_2=0$. Thereafter, the points assigned $w_2=0$ are eliminated from $P_v$.

Furthermore, to use the phenomenon in which, generally, the intensity near the center of a vessel is high while the intensity decreases in proportion to proximity to a blood vessel wall due to the density of blood flow and the partial volume effect, Laplacian $\nabla^2 I(v_i)$ is calculated from the fact that Laplacian comes to have a value other than 0 where scalar fields collide with each other, as a local intensity index. If this value is equal to or greater than 0.1, a region in question is determined to be a region where two blood vessels are close to each other. These points are assigned $w_2=0.5$, and thus connection via these points is prevented. The remaining points are assigned $w_2=1$. The w values calculated as described above are stored for future use.

2. Artery and Vein Classification

2. A. and B. Initial Tree Construction and Tree Structure Refinement

Figure 4:
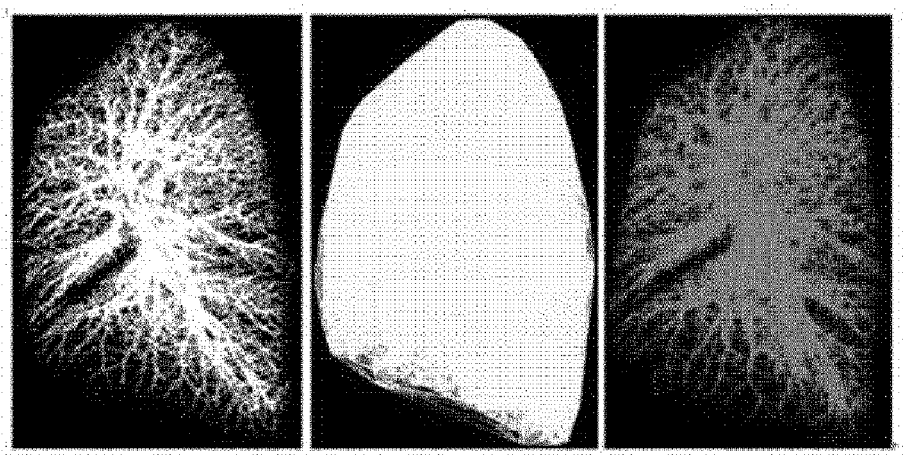
FIG. 4 is a view illustrating an example of the weight-based EMST according to the present disclosure.

One of the most important parts of the present disclosure is to construct an accurate tree structure that connects points, constituting the same type of vessels (veins or arteries), from $P_v$ by branches. For this process, in the present example, the weight-based Euclidean Minimum Spanning Tree (EMST) is used. In this case, the weight of the branch $e(u, v)$ connecting points u and $v \in P_v$ is calculated using $w_e=w_v/\|u-v\|$, where e is an ordered pair. The weight-based Delaunay triangulation (also called "regular triangulation using the CGAL library") is performed based on the fact (see [1]) that the EMST is a subset of the Delaunay triangulation (see [24]), and the weight-based EMST is calculated via the Dijkstra algorithm. ([1]: M. de Berg, M. van Kreveld, M. Overmars, O. Schwarzkopf, "Computational Geometry: Algorithms and Applications (2/E)," Springer, 1997; [24]: CGAL Library [Online], Available: http://www.cgal.org (URL)). FIG. 4 is a view illustrating an example of the weight-based EMST according to the present disclosure, wherein the left image shows an initial tree, the center image shows a weight-based Delaunay triangulated state, and the right image shows the weight-based EMST.

Figure 5:
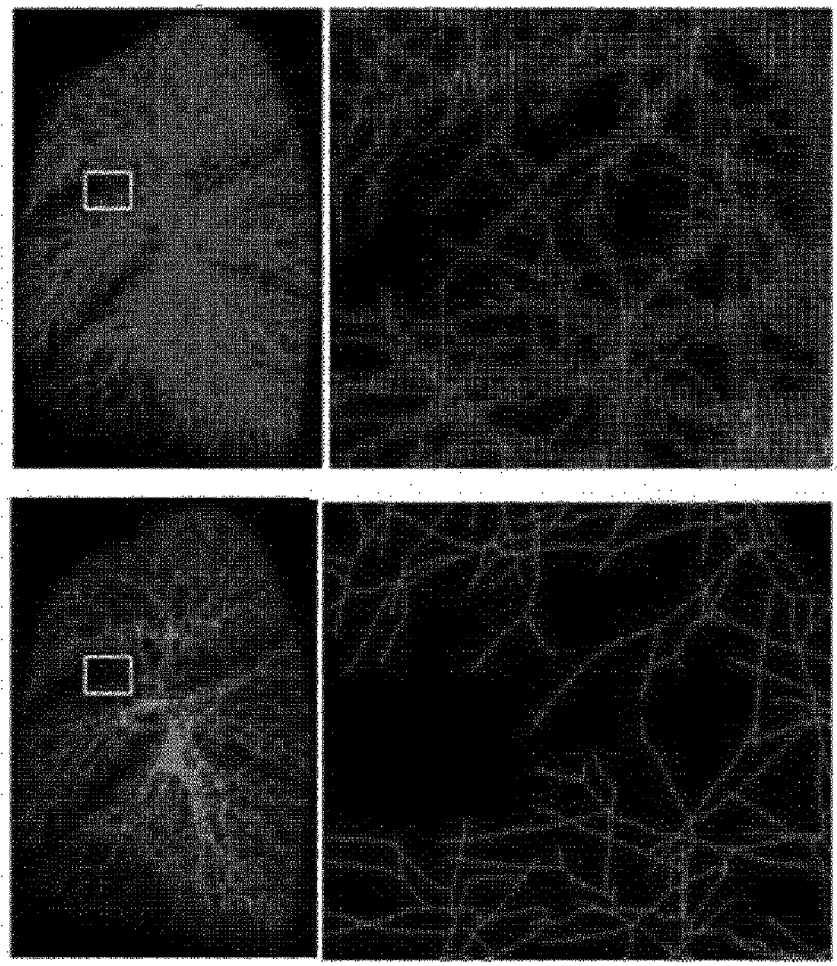
FIG. 5 is a view showing an example of a tree structure refined according to the present disclosure.

Thereafter, the refinement of the tree structure may be performed using a well-known method, such as a method presented by the paper by Livny (see [9]). ([9]: Y. Livny, F. Yan, M. Olson, B. Chen, H. Zhang, J. El-Sana, "Automatic reconstruction of tree skeletal structures from point clouds," ACM Transactions on Graphics, vol. 29(6), Article 151, 2010). FIG. 5 is a view showing an example of a tree structure refined according to the present disclosure, wherein an initial tree $T=(\{v\}, \{e\}, \{(v, e_v)\}$ (where $\{(v, e_v)\}$ is the incidence table of the initial tree T) is shown on the upper left side, an enlarged screen shot of the initial tree is shown on the upper right side, a refined tree T' is shown on the lower left side, and an enlarged screen shot of the refined tree is shown on the lower right side.

2. C. Splitting and Remerging

After all blood vessels have been connected to a single connected tree structure, individual branches may be automatically split by cutting off a region adjacent to a root to which all the branches are connected. For this purpose, labels are assigned such that the values thereof increase in a direction from each leaf edge of a tree to the root thereof, as shown in Equation 1, and then all the branches that belong to branches connected from a branch having the largest value and that have a difference in label within a predetermined value are cut off.

$$L(e) = \begin{cases} 1, & \text{if } e \text{ is a leaf edge} \\ \max\{L(e_c)\} + 1, & \text{otherwise} \end{cases} \quad (1)$$

where $e_c$ is the child edge of e.

Figure 6:
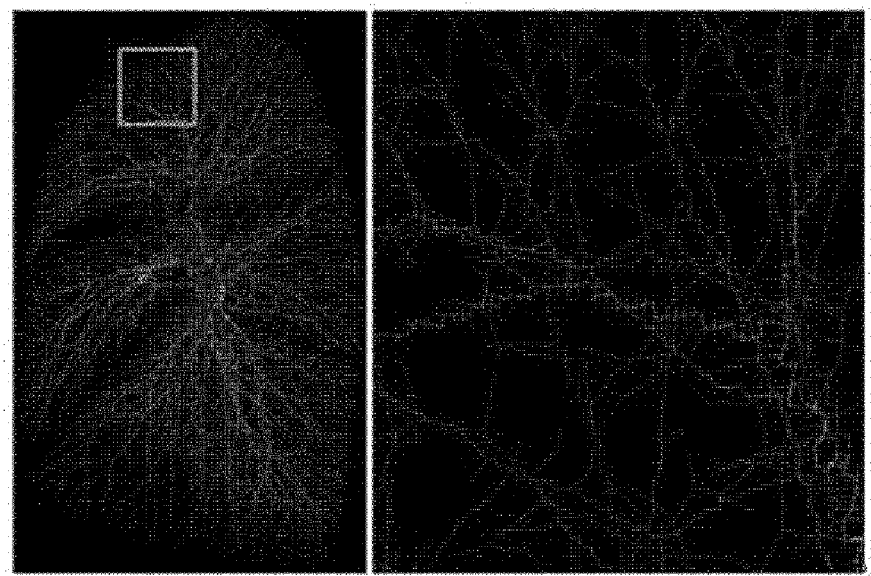
FIG. 6 shows images in which intensities have been assigned to branches according to label values.
Figure 7:
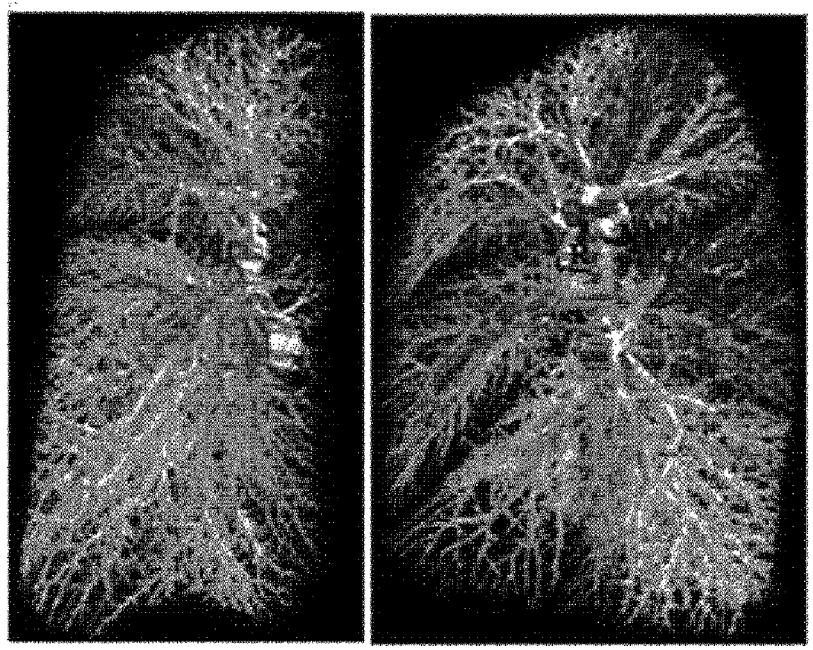
FIG. 7 shows 3D images of blood vessels split through splitting.

FIG. 6 shows images in which intensities have been assigned to branches according to label values, wherein a branch edge having a low label value has a dark gray color and the color becomes brighter as the label value increases. FIG. 7 shows 3D images of blood vessels split through splitting, wherein a tree is split into a plurality of regions by cutting off a mediastinal region (proximal region), and thus pulmonary arteries and pulmonary veins may be distinguished from each other.

Figure 8:
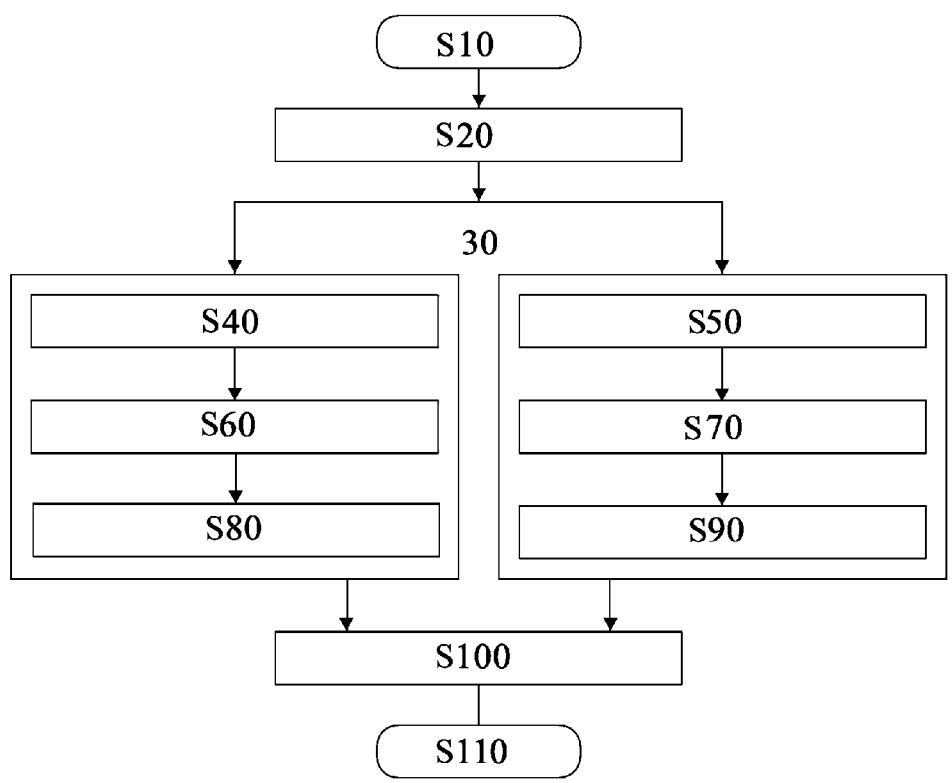
FIG. 8 is a diagram generally illustrating an example of a method for quantifying blood vessels according to the present disclosure.

FIG. 8 is a diagram generally illustrating an example of a method for quantifying blood vessels according to the present disclosure.

The method for quantifying blood vessels provides a method of observing a clinically significant region (a region of interest) in an organ and then quantifying length information including the diameters of blood vessels.

In the method for quantifying blood vessels, blood vessels are extracted as a 3D set of voxels based on medical images of an organ at step S10. The voxels of blood vessels included in a region of interest of the organ are found at steps S40, S60, S80, S50, S70 and S90. The length information of the blood vessels, including the diameters of the blood vessels, is quantified using the found voxels at step S100.

After the blood vessels have been extracted, the process of classifying the blood vessels into veins and arteries may be performed at step S20.

The length information of the blood vessels including the diameters may be visualized in a medical image at step S110.

For example, in the process of quantifying the length information of the blood vessels, the radii, i.e., diameters, of the blood vessels are calculated using the found voxels.

The ratio of the area of the blood vessels to the region of interest is calculated using the calculated radii of the blood vessels.

In the process of finding the voxels of the blood vessels, the levels of the blood vessels based on the shapes of the blood vessels or the locations of the blood vessels in the organ may be determined. The voxels of the blood vessels are found at a level selected as the region of interest.

For example, to find the voxels of the blood vessels, the skeletons of blood vessels are generated at step S40. Nodes at which blood vessels branch off are extracted using the skeletons of the blood vessels at step S60. Voxels within a predetermined spatial range around a node selected from the extracted nodes as a region of interest are found at step S80.

As a different example, to find the voxels of the blood vessels, offset surfaces defined as a set of voxels present within a predetermined distance from the outer surface of the organ to the inside thereof are generated at steps S50 and S70. Voxels corresponding to intersections between the extracted blood vessels and the offset surfaces are found at step S90.

The method for quantifying blood vessels according to the present disclosure may be applied to organs or parts of the human body, such as the lungs, the heart, the kidney, the liver, the brain, etc.

The present example is described with a focus on a method for quantifying pulmonary vessels.

For example, pulmonary vessels are extracted as a set of voxels from volumetric chest CT images, and an initial pulmonary vessel tree is generated using a construction energy minimization method. Thereafter, the branches of the initial pulmonary vessel tree are automatically split into sub-trees by cutting off a mediastinal region from the initial pulmonary vessel tree. Thereafter, the sub-trees are remerged by extending branches to the mediastinal region cut off from the branches of the initial pulmonary vessel tree. Thereafter, the pulmonary vessels are classified into pulmonary arteries and pulmonary veins based on the initial tree obtained through the remerging and, thus, classified pulmonary vessel trees are generated at step S20.

Once the classified pulmonary vessel trees have been generated, the pulmonary vessels may be visualized in the state of being classified into the pulmonary arteries and the pulmonary veins, and thereafter the basis 30 of the process of quantifying the length information of the pulmonary vessels is provided.

The length information of the pulmonary vessels, for example, the diameters of small pulmonary arteries and small pulmonary veins, are calculated from the voxels of the classified pulmonary vessel trees corresponding to a region of interest of the lungs. The ratio of the area of the small pulmonary arteries and the small pulmonary veins to the surface of the lungs in the region of interest of the lungs may be calculated using the diameters by means of an application.

In the present example, in order to extract the pulmonary vessels located in the region of interest, the levels of the pulmonary vessels are determined, and the length information of the pulmonary vessels having an identical or similar level is estimated.

In FIG. 8, two examples of the process of determining the levels of pulmonary vessels are shown.

In the process of determining the levels of pulmonary vessels according to an embodiment, the skeletons of the classified pulmonary vessel trees are calculated at step S40, pulmonary vessel branching nodes are extracted from the outer distal end of the lung at step S60, and pulmonary vessels having identical or similar levels may be collected at step S80.

In the process of determining the levels of pulmonary vessels according to another embodiment, offset surfaces are formed by gradually peeling the lung from the surface boundary of the lung at p S50, the intersections between the offset surfaces and the classified pulmonary vessel trees are extracted step S70, and pulmonary vessels having an identical or similar level (a distance level from the outer distal end of the lungs) may be extracted at step S90.

The pulmonary vessels having an identical or similar level extracted as described above are stored as a set of voxels 30, and become the basis of quantitative property estimation, such as the estimation of diameters or an area ratio.

Accordingly, the present disclosure discloses at least two embodiments of a method for quantifying blood vessels.

In a method for quantifying blood vessels according to an embodiment, classified pulmonary vessel trees are generated, the skeletons of the classified pulmonary vessel trees are formed, branching levels are determined and pulmonary vessels in a region of interest are extracted, and then length information is estimated.

In a method for quantifying blood vessels according to another embodiment, classified pulmonary vessel trees are generated, the offset surfaces of the lungs are formed, the intersections between the classified pulmonary vessel trees and the offset surfaces are extracted and pulmonary vessels in a region of interest are extracted, and then length information is estimated.

The two embodiments of the method for quantifying blood vessels all provide the quantified indices of pulmonary vessels. In some cases, the circulation state of pulmonary vessels may be more effectively and accurately estimated using the methods of the two embodiments together.

The process of generating classified pulmonary vessel trees is described first, and then two methods of determining and quantifying the levels of pulmonary vessels are described below.

Figure 9:
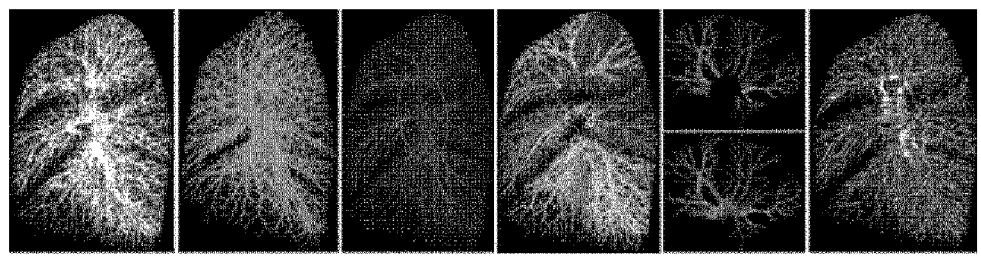
FIG. 9 shows views illustrating an example of the overall process of generating classified pulmonary vessel trees.
Figure 10:
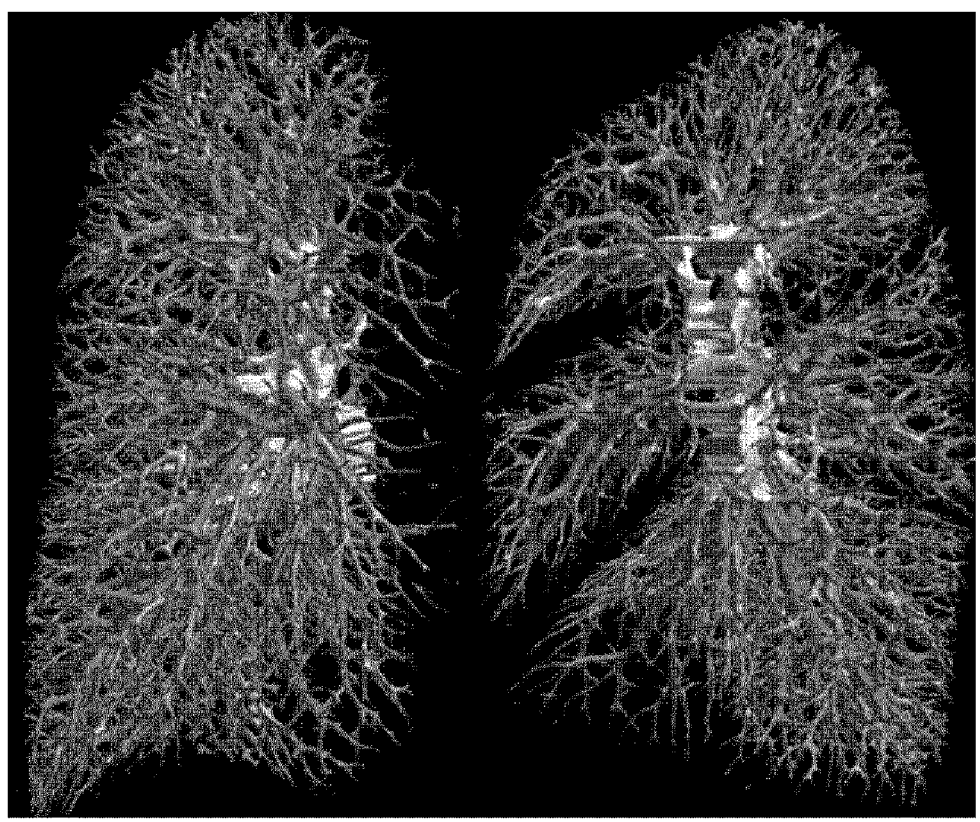
FIG. 10 shows views illustrating an example of classified pulmonary vessel trees.

FIG. 9 shows views illustrating an example of the overall process of generating classified pulmonary vessel trees. FIG. 10 shows views illustrating an example of classified pulmonary vessel trees.

In the order from the left of FIG. 9 to the right thereof, there is shown the process of: extracting pulmonary vessels from volumetric chest CT images as a set of points (point set extraction; see the first view); generating an initial tree using a construction energy minimization method (initial tree construction; see the second view); cutting off a mediastinal from the initial tree (cutting the mediastinal; see the third view); automatically separating the children branches of the initial tree into sub-trees (automatic separation of branches; see the fourth view); remerging the sub-trees by extending branches to the mediastinal cuf off from the branches of the initial tree (tree reconstruction and merging; see the fifth view); and classifying the pulmonary vessels into pulmonary arteries and pulmonary veins based on the remerged initial tree (artery and vein selection; see the sixth view).

In FIG. 10, the left view is a coronal view, the right view is a sagittal view, and the red color is representative of a pulmonary artery and the blue color is representative of a pulmonary vein.

A method of generating classified pulmonary vessel trees, such as those shown in FIGS. 9 and 10, is described using equations below.

In order to quantify small pulmonary arteries and pulmonary veins, it is preferable to split and classify small pulmonary arteries and pulmonary veins. A method of classifying pulmonary vessels is described briefly below.

$$\Gamma=\{c|c=((i, j, k), i=1, \ldots, nx, j=1, \ldots, ny, k=1, \ldots, nz\}$$

is set to a set of voxels constructed from CT scan images, and $I(c)$ is set to the attenuation intensity of a voxel $c$. First, vascular points $V=\{v_i\} \subset R3$ are extracted. In this case, $v(c)=(x, y, z)^T=((c_i-0.5)\times dx,(c_j-0.5)\times dy,(c_k-0.5)\times dz)^T$ is the center location of the corresponding voxel $c$. Then different types of voxels may be classified by constructing an initial tree T=E). In this case, E is a set of edges. The initial tree is constructed by a minimizing cost method defined by Equation 2 below:

$$\min_T C(T) = \min_E \sum_{(i,j)\in E} C(i,j) = \min_E \sum_{(i,j)\in E} \frac{\|v_j - v_i\|}{\alpha + \beta w_j + \gamma e_{ij}} \quad (2)$$

where $w_j$ is the weight of vertex j, $e_{ij}$ is the directional weight of edge (i, j), and $\alpha, \beta, \gamma \in R$ is positive user-defined constants. $w_j$ is a value representative of the connection characteristic of vertex j, and is defined as $w_j = I(vj) + |\Phi(vj)| + \min\{1, 1-\nabla^2\Phi(v_j)\}$. $I(vj)$ is the attenuation intensity of vj standardized by all vascular points, and $\Phi(vj)$ is a distance standardized from the boundaries of the blood vessels. $e_{ij}$ is a factor representative of directional similarity between vascular orientations estimated based on the directions of the edges and vj.

A solution to the minimization of Equation 1 naturally becomes the minimum spanning tree (MST).

After the initial tree has been constructed, a mediastinal region is cut off. Branches are split from each other by grouping only connected vertices, and thus sub-trees are automatically formed.

T=(Vi, Ei) ⊂ T is set to the i-th sub-tree of T. Prior to cutting off, the orientation vectors $\{o_i\}$ of all the vertices are re-estimated by performing global optimization adapted to minimizing Equation 3 derived from the paper by Livny et al, "Automatic reconstruction of tree skeletal structures from point clouds," ACM Transactions on Graphics, vol. 29(6), Article 151, 2010.

$$\min_0 \{\Delta E(T) + \Delta O(T)\} \quad (3)$$

$$\Delta E(T) = \sum_{v_i \in V} \left( w_i \left\| o_i - \frac{(v_i^p - v_i)}{\|v_i^p - v_i\|} \right\| \right)^2,$$

$$\Delta O(T) = \sum_{v_i \in V} \left( \frac{w_i^p + w_i}{2} \|o_i^p + o_i\| \right)^2$$

where $v_i^p$ is the parent vertex of vi.

The groups are extended from each root vertex to a region whose end is cut off using $\{o_i\}$, and are remerged if there is no overlapping branch. Finally, the types of blood vessels (artery type and vein type) are determined based on the remerged pulmonary vessel tree by a user interface, and thus classified pulmonary vessel trees are generated. The classified pulmonary vessel trees are stored as $T_A$ and $T_V$ for use at subsequent steps.

As described above, the length information of the blood vessels including the diameter of the lung is quantified based on the classified pulmonary vessel trees, and the levels of the pulmonary vessels are determined for the purpose of performing the quantification. Of methods of determining the levels of pulmonary vessels, a method using the branching levels of pulmonary vessels is described below.

Figure 11:
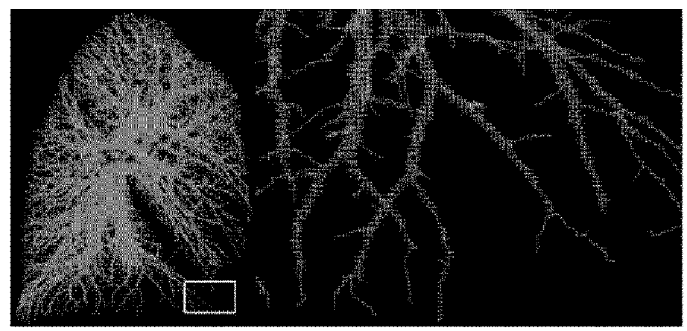
FIG. 11 shows views illustrating an example of the result of an algorithm for obtaining the skeletons of classified pulmonary vessel trees and extracting nodes.
Figure 11:
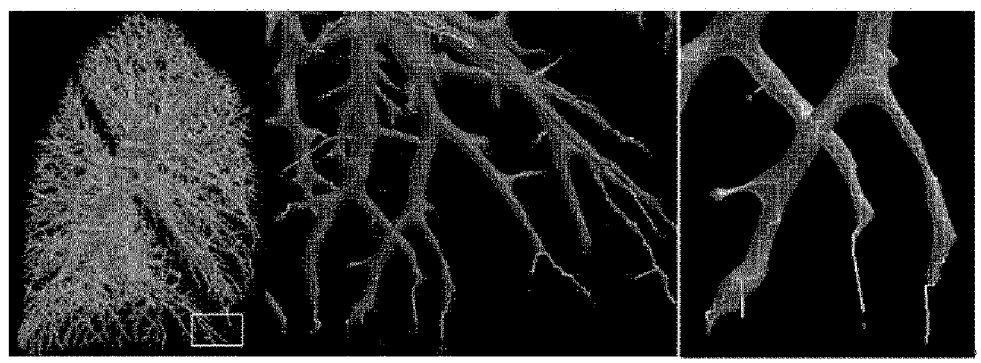

FIG. 11 shows views illustrating an example of the result of an algorithm for obtaining the skeletons of classified pulmonary vessel trees and extracting nodes.

In order to determine branching levels, the skeletons of classified pulmonary vessel trees are obtained (at step S40 of FIG. 8), and nodes are extracted (at step of S60 of FIG. 8).

Obtaining the skeleton of the pulmonary vessels using given geometrical computation is a massive task. An automated method of extracting medial lines by calculating outward flux is disclosed in the paper by Bouix et al., "Flux driven automatic centerline extraction," Medical Image Analysis, vol. 9, pp. 209-221, 2005. Furthermore, a curve skeleton construction algorithm using a gradient vector flow is disclosed in the paper by Hassouna et al., "Variational curve skeletons using gradient vector flow," IEEE Transactions on Pattern Analysis and Machine Intelligence, vol. 31, no. 12, pp. 2257-2274, 2009. Furthermore, a method of reconstructing surfaces by extracting curve skeletons from point clouds including big points regardless of a medical application is disclosed in the paper by Tagliasacchi et al., "Curve skeleton extraction from incomplete point cloud," ACM Transactions on Graphics, vol. 28(4), Article 71, 2009. Furthermore, a method of successfully reconstructing surfaces from unorganized point clouds and noise by introducing an arterial snakes concept is disclosed in the paper by Li et al., "Analysis, reconstruction and manipulation using arterial snakes," ACM Transactions on Graphics, Vol. 29(6), Article 152, 2010.

In the present embodiment, the skeletons of trees may be obtained using a simpler method different from the above-described methods of obtaining skeletons. The reason for this is that in the present disclosure, skeletons are obtained using the above-described classified pulmonary vessel trees, and thus the present embodiment does not start with raw data, such as point clouds or voxels.

More specifically, to obtain skeletons, the present embodiment finds branching locations, rather than calculating smooth curve skeletons. For example, medial lines are extracted from the above-described classified pulmonary vessel trees (the upper view of FIG. 11), and nodes to which two or more children edges are connected are found (the lower center view of FIG. 11). The medial lines (in the present disclosure, called a "skeleton") of cylindrical regions may be extracted using Equation 4 similar to parallel thinning algorithms (disclosed in the paper by Bertrand et al., "A parallel thinning algorithm for medial surfaces," Pattern Recognition Letters, vol. 16(9), pp. 979-986, 1995).

Prior to cutting off a mediastinal region (proximal region) in the process of generating the above-described classified pulmonary vessel trees, inverse height values are assigned to all vertices v∈V of the MST, as shown in Equation 4 below:

$$H(v) = \begin{cases} 0, & \text{if } v \text{ is a leaf edge} \\ \max\{H(v_c) + \|v_c - v\|\} + 1, & \text{otherwise} \end{cases} \quad (4)$$

In this equation, $v_c$ is the child node of v, and the ones of the child nodes $C(v)=\{v_c\}$ of a certain non-leaf node v∈V that correspond to $v_c^* = \arg\max\{H(v_c)+\|v_c-v\|\}$ are set to critical nodes. In this case, the accumulated inverse height of the critical nodes for v is a maximum value. The children nodes other than V*C are set to non-critical nodes. A skeletal structure may be extracted by eliminating the non-critical nodes.

For example, non-critical nodes that satisfy any one of the following conditions are eliminated from leaf nodes:

a) leaf node;
b) $H(vc) \geq \alpha|\Phi(v)|$: whose path length is shorter than the scaled radius of the parent node $\alpha|\Phi(v)|$; or
c) $H(vc) < \beta$: whose path length is shorter than a user-defined threshold β.

In the present embodiment, α=1.2 and β=3.0 mm are used. When nodes are eliminated, connected child critical nodes and edges are also eliminated, and the remaining connected paths become a skeleton (see the lower right view of FIG. 11).

FIG. 11 shows the result of an algorithm for obtaining a skeleton while eliminating nodes, as described above. This algorithm does not ensure that a result connected to single line segments is provided in a mediastinal region having a non-cylindrical shape depending on parameters α and β. However, this algorithm is suitable for the purpose of the present disclosure that is to quantify the morphological characteristics of small blood vessels.

In a subsequent process, in order to estimate the radii of branches, it is necessary to collect vascular points having the same index of a single group (at step S80 of FIG. 8). For this purpose, in the algorithm, an ordered pair (i, j) is assigned to the j-th child branch of an i-th sub-tree, and ordered pairs are assigned to connection points whenever a branch of a skeleton branches off.

Figure 12:
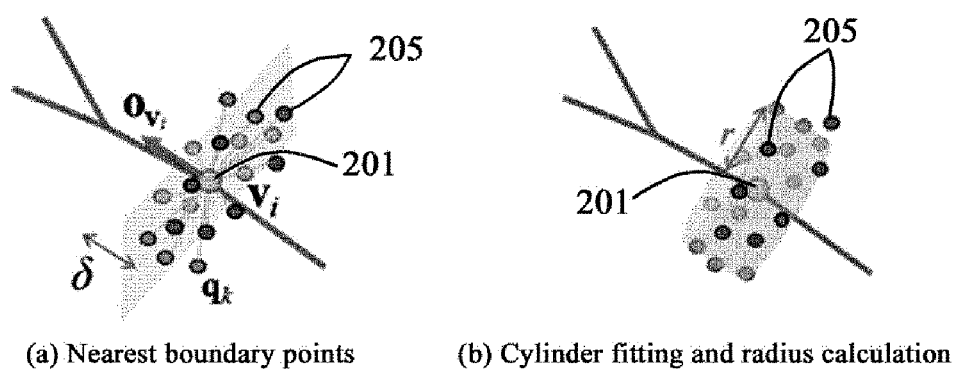
FIG. 12 shows diagrams illustrating an example of a method for quantifying blood vessels using nodes according to an embodiment of the present invention.

FIG. 12 shows diagrams illustrating an example of a method for quantifying blood vessels using nodes according to an embodiment of the present invention.

k-nearest boundary points $N_b(v_i)=\{q_j|j=1, k\} \subset \partial V$ at respective nodes $v_i$ of classified pulmonary vessel trees T may be collected as the same group using the ordered pairs, thereby enabling same level small pulmonary arteries and pulmonary veins corresponding to a region of interest to be extracted as the points of voxels.

In this case, the points collected as the same group satisfy $$\left|\frac{q_k - v_i}{\|q_k - v_i\|} \cdot o_{v_i}\right| < \delta,$$

where δ is a user-defined parameter. In FIG. 12(a), gray points 205 connected to a node vi 201 are representative of $N_b(v_i)$. In the tests of the present example, k=26 and β=π/4 are used.

The classified pulmonary vessel trees T are used to collect spatially close points in a voxel structure. The radii of branches at nodes may be obtained by performing cylinder fitting using the simple least-squares method based on $N_b(v_i)$, as shown in FIG. 12(b) (see the paper by D. Eberly, "Fitting 3D data with a cylinder," [Online] February 2003. Available: http://www.geometrictools.com/Documentation/CylinderFitting.pdf(URL)).

When the number of the neighbor points of a certain node is less than 10 and insufficient because original blood vessels are excessively thin, $\tilde{\gamma}(v_i)$ included in Equation 5 below is used as a radius. When there are no neighbor points, calculation is performed with the radius of a corresponding node set to a half of the size of CT resolution. For example, since the resolution of CT images ranges from about 0.545 to 0.693 mm, rmin=0.3 mm is used for data that is used for a radius estimation task.

$$\tilde{\gamma}(v_i) = \frac{1}{k}\sum_{j=1}^{k}\left\|q_j - \frac{(q_k - v_i)}{\|q_k - v_i\|} \cdot o_{v_i}\right\| \tag{5}$$

Figure 13:
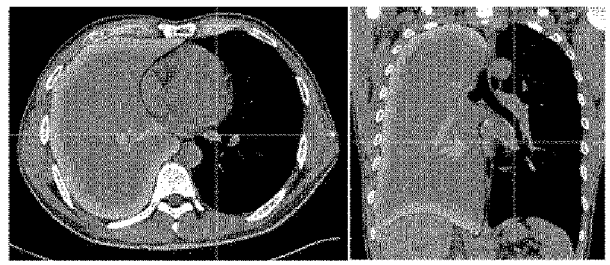
FIG. 13 shows views illustrating an example of a method for quantifying blood vessels using offset surfaces according to another embodiment of the present disclosure.
Figure 13:
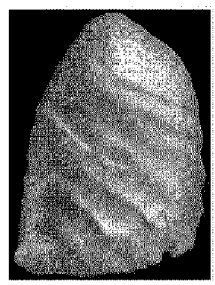
Figure 13:
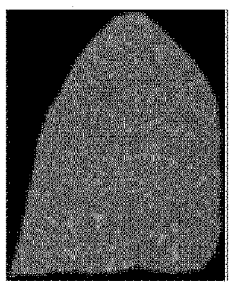
Figure 13:
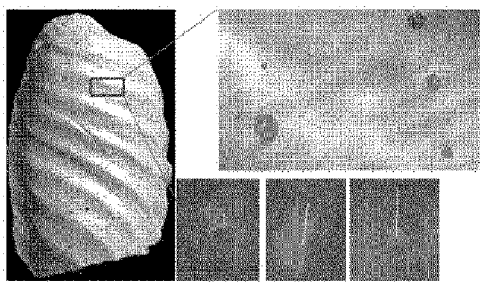

FIG. 13 shows views illustrating an example of a method for quantifying blood vessels using offset surfaces according to another embodiment of the present disclosure.

FIG. 13 is described in conjunction with FIGS. 14 to 19 in detail.

Figure 14:
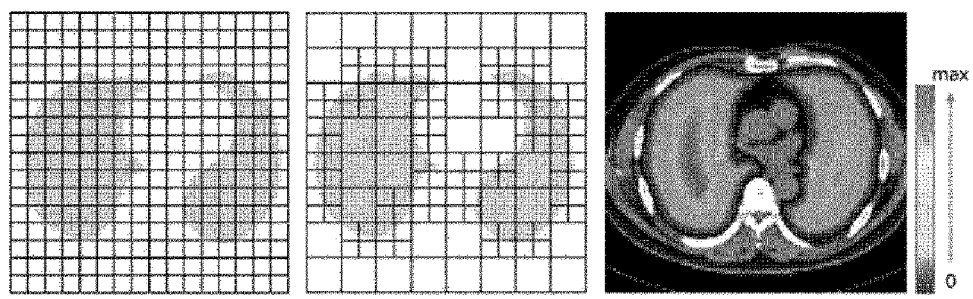
FIG. 14 shows views illustrating an example of a method of generating a distance field in order to form offset surfaces.
Figure 14:
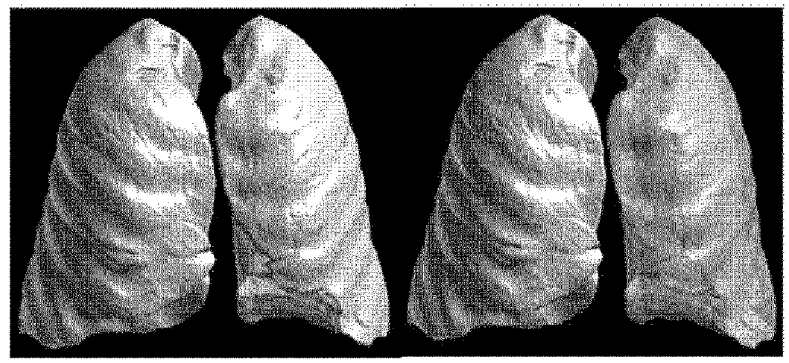

FIG. 14 shows views illustrating an example of a method of generating a Euclidean distance field in order to form offset surfaces.

As a method of determining the levels of small pulmonary vessels in order to quantify pulmonary vessels, there is described a method of collecting small pulmonary vessels having the same level by using the geometry of the lung and estimating length information, unlike the above-described method of determining the branching level of blood vessels (the method using the shapes of blood vessels).

According to the fact that pulmonary vessels extend their branches from the inside of the body to distal regions, it may be assumed that there are similarly sized blood vessels within the same distance from the outer distal boundary surfaces of the lungs. Therefore, intersections are found between blood vessels exclusive of those of a mediastinal region and the inner surfaces of the lungs present within a predetermined distance from the outer distal boundary surfaces of the lungs, and the diameters of blood vessels are estimated at these intersections.

In order to obtain the intersections, it is necessary to gradually extract inner surfaces (see FIG. 13(a)). The inner surfaces of the lungs present within the predetermined distance from the outer distal boundary surfaces of the lungs becomes offset surfaces at the distance. The offset surfaces may be generated using a surface data calculation method generally more time efficient than a volume-based method, like face-based offset surfaces or vertex-based offset surfaces.

However, the above-described surface data calculation methods are vulnerable to local and global interference that occurs frequently when the surfaces of the lungs are internally offset. In particular, in the case of the present embodiment, an offset distance ranges from 5 to 30 mm. This distance is considerably longer than the length of a surface extracted from CT images using marching cubes, and thus interference is unavoidable. Therefore, in the present embodiment, offset surfaces are generated using a volume-base method that generates Euclidean distance fields (see FIG. 14(a)).

In the process of generating the above-described classified pulmonary vessel trees, the right and left lungs are clearly segmented into LR, LL ⊂ Γ before blood vessels are extracted as voxels (see the paper by Hu et al., "Automatic lung segmentation for accurate quantitation of volumetric X-ray CT images," IEEE Transactions on Medical Imaging, vol. 20 6, pp. 490-498, 2001).

For the LR and LL, Euclidean distance fields are generated from the boundaries of the LR and the LL, and iso-surfaces are extracted at required offset distances do (see FIG. 14(b)). In this case, do ∈ {5, 10, 15, 25, 30} in millimeter units were used in the tests of the present embodiment (see FIG. 13(a)).

For calculation efficiency, an octree structure is generated in order to generate Euclidean distance fields in which voxels correspond to the finest level of an octree, as shown in FIG. 14(a). When high spatial resolution is required only in a local region, the octree becomes a desirable data structure.

For example, when dmin(c, ∂L)<do<dmax(c, ∂L) is satisfied and only when it is satisfied, a single cell from root cells is refined into eight children. In this case, dmin(c, ∂L) and dmax(c, ∂L) are minimum and maximum distances, respectively, at the eight corners of a pixel c from ∂L, i.e., the boundary of L=LR ∪ LL. The results are set to voxels $S_R(do) \subset R$ and $S_L(do) \subset LL$ that satisfy dmin(c, ∂L)< do<dmax(c, ∂L) for the left and right lungs. A detailed execution method of generating distance fields using an octree can be found in the paper by Frisken et al., "Adaptively sampled distance fields: A general representation of shape for computer graphics," Proceedings of ACM SIGGRAPH, pp. 249, 254, 2000.

Iso-surfaces are extracted from the above-described Euclidean distance fields in the form of a triangular mesh (see FIG. 14(b)). The triangular mesh is calculated using a known marching cubes algorithm, and this calculation process may be time-efficiently performed through parallel computing using graphic processing units (CPUs).

Figure 15:
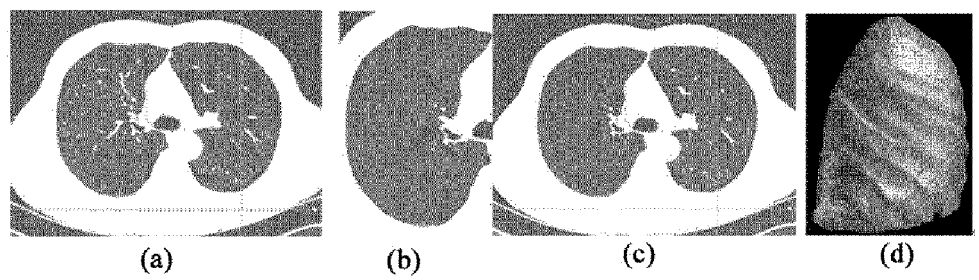
FIG. 15 shows views illustrating an example of the process of extracting intersections between inner surfaces and pulmonary vessels.

FIG. 15 shows views illustrating an example of the process of extracting intersections between inner surfaces and pulmonary vessels.

After the iso-surfaces are extracted in the form of a triangular mesh and inner surfaces, i.e., offset surfaces, are obtained at a specific distance, intersections between the offset surfaces and small pulmonary vessels are found. For this purpose, the offset surfaces are calculated using surface voxels S extracted as shown in FIG. 15 (see FIG. 15(a)). The method of extracting the skeletons of classified pulmonary vessel trees has been described above. In FIG. 15, the bit-mask of pulmonary vessels is shown as the skeleton of a tree bit-wised to Γ (see FIGS. 13(b), 13(c), 15(b), 15(c), and 15(d)). Accordingly, the intersections are simply obtained by checking the intersections between the surface voxels S and the skeleton of the tree bit-wised to Γ (see FIGS. 13(d) and 15(d)).

Figure 16:
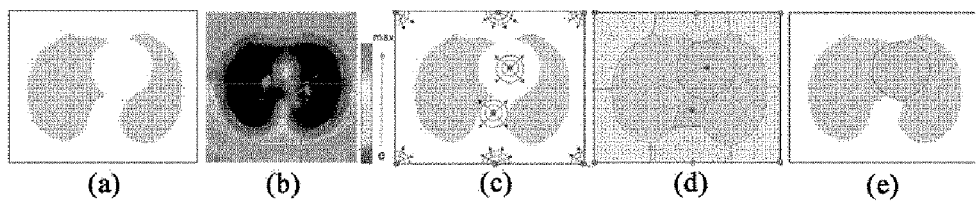
FIG. 16 shows views illustrating an example of the process of extracting a mono-oriented region for the segmentation of the lungs by using 2D schematic views.

FIG. 16 shows views illustrating an example of the process of extracting a mono-oriented region for the segmentation of the lungs by using 2D schematic views.

Since the present example is interested in the distal regions of the lungs (see FIG. 16(a)), it is necessary to avoid measuring the length information of the pulmonary vessels (for example, diameters) in a mediastinal region. Mono-oriented region partition may be used to find a region in which the measurement of length information can be avoided.

For example, active contours (see FIG. 16(c)) from the local maximum points of an outward distance field (see FIG. 16(b)) are generated from ∂L. The active contours move around through adjacent neighbor cells at the same speed using method of maintaining the same distance until they collide with other active contours or ∂L. Outer regions Γ/L are a group of cells propagated from the same speed point, and are partitioned into the number of local maxima. The result of this algorithm becomes the Voronoi diagram of ∂L.

The most mediastinal region of the lungs encompasses the inside of the chest cavity. Therefore, a region included in the mediastinal region may be extracted as M ⊂ Γ by eliminating a blue region (whose seed points are the corners of Γ), a green region (which includes the boundary cells of Γ) and an intersection region (which is a region including the ribs or the spine that can be easily partitioned by simple thresholding) in FIG. 16(b) (see FIGS. 16(d) and 16(e)).

Figure 17:
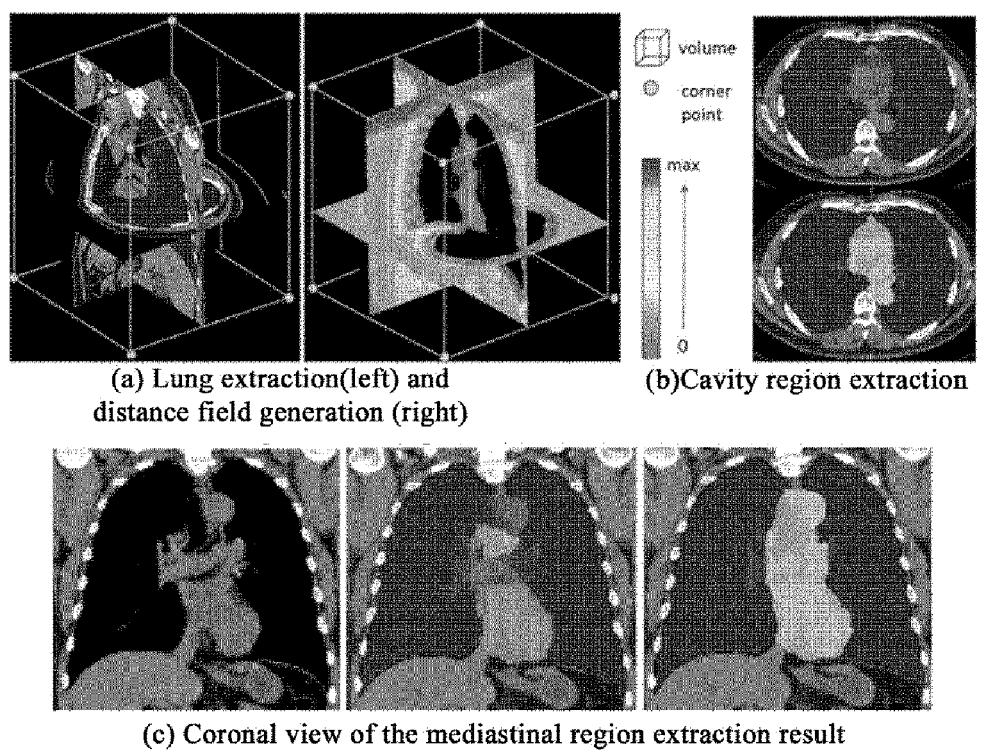
FIG. 17 shows views illustrating an example of mediastinal region extraction applied to volumetric CT images.

FIG. 17 shows views illustrating an example of mediastinal region extraction applied to volumetric CT images.

For the efficiency of calculation and effectiveness for the small features of pulmonary shapes, an octree is also used in the present example. FIG. 17 shows a result of a resolution, i.e., 128×128×128, down-sampled from 512×512×512 of original images for the purpose of the efficiency of computer calculation. The mediastinal region of the boundary surfaces of the lungs becomes ∂L∩M. When $S_R(d^o)$ and $S_L(d^o)$ are obtained, a distance may be calculated from ∂L/(∂L∩M).

Figure 18:
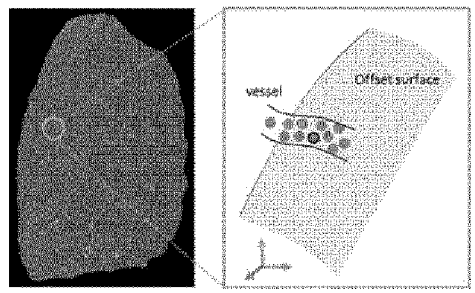
FIG. 18 shows views illustrating an example of surfels calculation.
Figure 18:
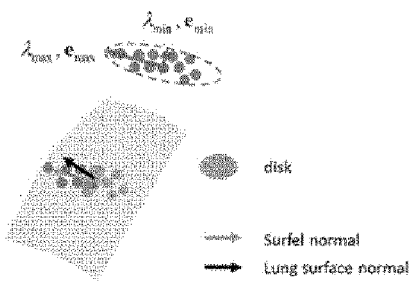
Figure 19:
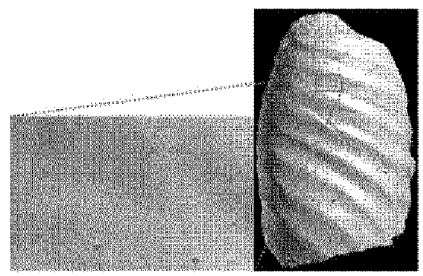
FIG. 19 shows views illustrating an example of surfels calculated through 3D rendering.
Figure 19:
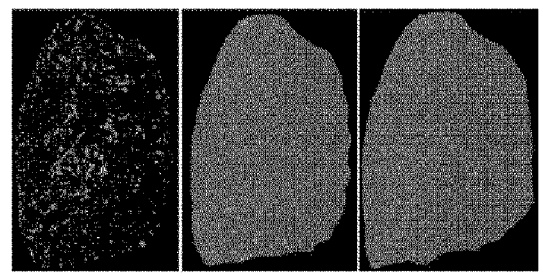

FIG. 18 shows views illustrating an example of surfels calculation, and FIG. 19 shows views illustrating an example of surfels calculated through 3D rendering.

Prior to the construction of an initial tree T, global optimization is performed using the above-described Equation 2, and also orientation vectors are estimated by performing basic component analysis on small blood vessels. The results of the estimation of the orientation vectors are stored as surface elements called "surfels." The surfels may be viewed as a circular disk having a normal vector and a radius on offset surfaces.

Regions requiring no quantification are eliminated from intersections (see the description of FIG. 15 and FIG. 18(a)) between the offset surfaces and the classified pulmonary vessel trees in order to estimate the length information of the small pulmonary vessels (for example, diameters) (see the descriptions of FIGS. 16 and 17).

Meanwhile, the branches of the classified pulmonary vessel trees do not always pass through the offset surfaces orthogonally. Accordingly, in order to obtain the diameters or areas of the branches of the classified pulmonary vessel trees, the branches of the classified pulmonary vessel trees may be orthogonally projected into the offset surfaces and then offset areas, i.e., the sectional areas of the blood vessels, may be calculated on the offset surfaces (see FIG. 18(b)).

In this case, the surfels reflect the orientations of the branches of the classified pulmonary vessel trees, and thus the radii of the small pulmonary vessels may be estimated in a direction orthogonal to the branches of the pulmonary vessel tree using the offset areas and the normal vector of the surfels.

The average areas of small pulmonary arteries and pulmonary veins may be calculated using the estimated radii of the small pulmonary vessels, and also cross-sectional areas between the small pulmonary vessels and the offset surfaces may be measured on the offset surfaces (see FIG. 19).

For the tests of the method for quantifying blood vessels according to the present example, the non-contrast volumetric chest CT scan images of 25 COPD patients, which had a thickness ranging 0.545 to 0.693 mm, were used. An algorithm that was used in the tests did not depend on a respiratory step, but used a sufficient number of images to perform consistent comparison.

In the classification of pulmonary vessels, the method for quantifying blood vessels according to the present disclosure was evaluated using a mathematical virtual model and the preceding research of experts (see the paper by Park et al., "Automatic classification of pulmonary artery and vein by tree reconstruction at volumetric chest CT," Submitted, 2013).

The average score values of respective segments are listed in Table 1.

The tests were conducted on a software platform developed to perform the method for quantifying blood vessels according to the present example, and Microsoft Visual C++(10.0) was used as a host program because a device program for parallel computing using GPUs was written in nVidia CUDA 5.0 SDK. A test environment for the tests was a desktop PC composed of nVidiaQuadro 600 (1 GB), 12 GB main memory, Intel Core i7 960 (3.2 GHz) to perform parallel computing.

Figure 20:
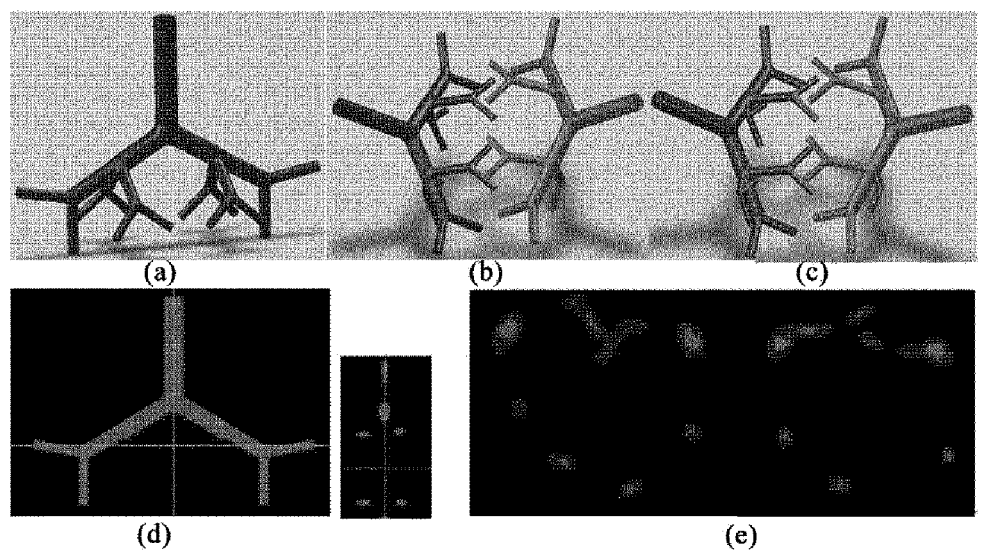
FIG. 20 shows views illustrating the accuracy of radius estimation using virtual vascular phantom models.

FIG. 20 shows views illustrating the accuracy of radius estimation using virtual vascular phantom models.

To measure the accuracy of the calculation of vessel radii, a virtual model is generated. FIG. 20(a) shows a single vascular tree mode aligned with global coordinates, and FIG. 20(b) shows an assembled vascular phantom model.

The error in the estimation of the radii was 0.101±0.042mm (mean±SD) at 70 sampled positions for the single model and 0.137±0.055 mm (mean±SD) at 140 points of the coupled model (see FIG. 20(c)). This is viewed as acceptable accuracy.

Table 1 shows characteristics estimated at branching nodes from a vascular skeleton, and Table 2 shows the results of gradual peeling.

In the tests, as shown in Tables 1 and 2, there is a tendency for the diameters of pulmonary veins to have greater deviations than the diameters of pulmonary arteries. In Table 2, although the number of calculated veins is smaller than the number of calculated arteries in terms of average, the area percentages thereof are almost similar to each other. As to the area percentage of the pulmonary vessels in the surface of the lungs, there is a tendency for both the area percentages of arteries and veins to increase up to a location of 30 mm in an inward direction.

TABLE 1

Morphological properties based on branching levels

| Branch | Artery | | | Vein | | |
|---|---|---|---|---|---|---|
| level | NO* | MEAN_D | STD_D | NO | MEAN_D | STD_D |
| 1st | 630.20 | 1.895 | 0.112 | 601.72 | 1.912 | 0.220 |
| 2nd | 413.17 | 1.956 | 0.131 | 402.29 | 2.014 | 0.312 |
| 3rd | 305.39 | 2.135 | 0.133 | 299.32 | 2.251 | 0.223 |
| 4th | 242.18 | 2.412 | 0.142 | 220.13 | 2.481 | 0.412 |

In this table, NO is the total number of vessels, MEAN_D is the mean of diameters, and STD_D is the standard deviation of diameters.

TABLE 2

Morphological properties in the case of gradual peeling

| | | Offset Level do (mm) | | | | | |
|---|---|---|---|---|---|---|---|
| | Properties | 5 | 10 | 15 | 20 | 25 | 30 |
| Artery | NO | 929.06 | 857.00 | 735.71 | 678.70 | 573.24 | 454.35 |
| | MEAN_D (mm) | 1.541 | 1.835 | 1.921 | 1.975 | 1.975 | 2.073 |
| | STD_D | 0.213 | 0.113 | 0.121 | 0.131 | 0.125 | 0.136 |
| | W_AREA* (mm2) | 2.241 | 3.462 | 3.507 | 3.772 | 3.682 | 4.050 |
| | CR_AREA (mm2) | 2.780 | 3.771 | 3.891 | 4.013 | 4.152 | 4.413 |
| | % | 1.98 | 2.30 | 3.21 | 3.75 | 4.10 | 4.45 |
| Vein | NO | 779.47 | 794.29 | 650.82 | 574.29 | 503.18 | 422.38 |
| | MEAN_D (mm) | 1.761 | 1.882 | 1.975 | 2.063 | 2.073 | 2.132 |
| | STD_D | 0.979 | 0.201 | 0.206 | 0.270 | 0.306 | 0.800 |
| | W_AREA (mm2) | 2.931 | 3.615 | 3.676 | 4.151 | 4.429 | 4.462 |
| | CR_AREA (mm2) | 3.316 | 3.914 | 4.014 | 4.443 | 4.913 | 4.902 |
| | % | 1.98 | 2.66 | 2.93 | 3.28 | 3.83 | 4.52 |

In this table, W_AREA is a weighted average area, CR_AREA is the mean of the cross-sectional areas between vessels and inner surfaces, and % is the area percentage of the vessels (=CR_AREA×NO /area of S(d$^o$)).

Figure 21:
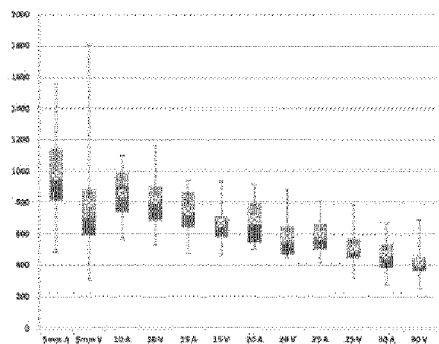
FIG. 21 shows box plots illustrating the numbers of blood vessels, the average diameters of blood vessels, and the area percentages of blood vessels according to gradual peeling and tree branching levels.
Figure 21:
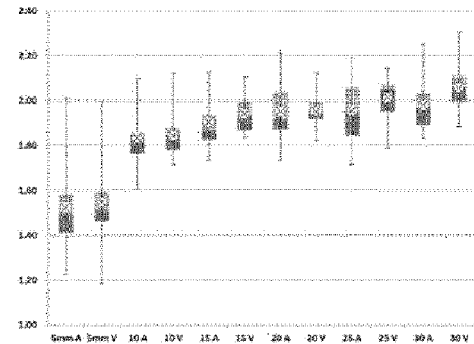
Figure 21:
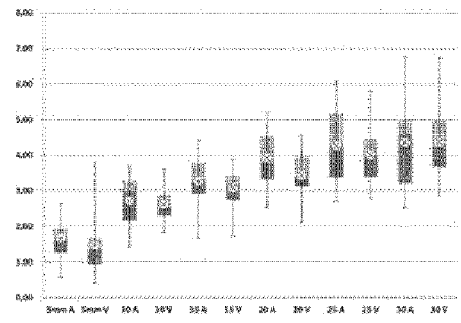
Figure 21:
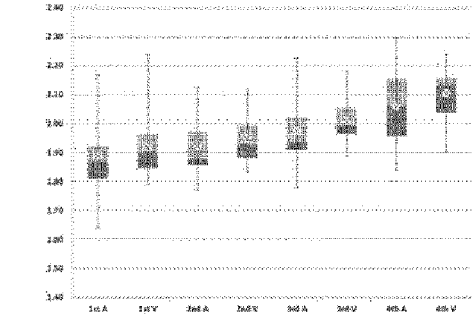

FIG. 21 shows box plots illustrating the numbers of blood vessels, the average diameters of blood vessels, and the area percentages of blood vessels according to gradual peeling and tree branching levels.

In FIG. 21, red boxes are located between a quartile and a median, green boxes are located between the median and a third quartile, and yellow points are representative of mean values.

In FIG. 21, although statistical meanings need to be compared with clinical parameters, morphological tendencies may be observed from these graphs. For example, the rate of increase in diameter undergoes a sharp slope and then gradually becomes moderate in the direction of a mediastinal region according to gradual peeling. Meanwhile, the slope of an average radius changes almost linearly along the branches of a tree up to a 4th level.

Various embodiments of the present disclosure are described below:

(1) The method for distinguishing between pulmonary arteries and pulmonary veins, wherein the tree is formed by a weight-based EMST technique.

(2) The method for distinguishing between pulmonary arteries and pulmonary veins, wherein the tree is formed by connecting the points in the set of pulmonary vessels Pv to a branch e(u, v) (where u and v are points inside Pv), and the weight of the branch e(u, v) is calculated using $w_e = w_v/\|u-v\|$ (where $w_v$ is the weight information of v).

(3) The method for distinguishing between pulmonary arteries and pulmonary veins, wherein the weight information w is calculated using $w = w_1 \times w_2$, $w_i$ is an intensity weight and is defined as $(i - i_{min})/(i_{max} - i_{min})$, and $w_2$ is a local shape weight.

(4) The method for distinguishing between pulmonary arteries and pulmonary veins, wherein a relatively low local shape weight is assigned to each of points located between other vessels.

(5) The method for distinguishing between pulmonary arteries and pulmonary veins, wherein the set of pulmonary vessels Pv is given as {v(c)}, and v(c) is a vector composed of the center coordinate of a cell c and the weight information and is defined as $v = (x, y, z, w)^T = (v_p^T, w)^T$, where $V_p = (x, y, z)^T = ((c_i - 0.5)d_x, (c_j - 0.5)d_y, (c_k - 0.5)d_z)^T$.

(6) The method for distinguishing between pulmonary arteries and pulmonary veins, wherein the separating the tree into a plurality of a plurality of regions includes assigning label values that increase in a direction from the leaf edge of each branch from a root and then eliminating branches having a large label value.

(7) The method for distinguishing between pulmonary arteries and pulmonary veins, wherein the forming a tree includes performing weight-based Delaunay triangulation and then applying the Dijkstra algorithm.

(8) The method for quantifying blood vessels, wherein the quantifying the length information of the blood vessels includes: calculating the radii of the blood vessels using the found voxels; and calculating the area ratio of the blood vessels to the region of interest using the calculated radii of the blood vessels.

The length information of the blood vessels may refer to not only the radii and diameters of the blood vessels but also the widths or thicknesses of the blood vessels, which cannot be represented using diameters or radii. In some cases, the length information of the blood vessels may refer to the vascular lengths of the blood vessels orthogonal to the radial direction of the blood vessels. Once the radii of the blood vessels have been determined, quantitative values, such as the cross-sectional areas of the blood vessels and the area ratio of the cross-sectional areas of the blood vessels to a specific offset surface of the organ, may be extracted.

(9) The method for quantifying blood vessels, wherein the finding the voxels of blood vessels includes: determining the levels of the blood vessels based on the morphological characteristics of the blood vessels or the locations of the blood vessels in the organ; and finding the voxels of the blood vessels at a level selected as the region of interest.

(10) The method for quantifying blood vessels, wherein the finding the voxels of blood vessels includes: extracting the medial lines of the extracted blood vessels; finding voxels along medial lines included in the region of interest; and finding neighbor boundary voxels from the voxels along the medial lines.

(11) The method for quantifying blood vessels, wherein the finding the voxels of blood vessels includes: generating the skeletons of the blood vessels by extracting the medial lines of the blood vessels; extracting nodes, at which blood vessels branch off, using the skeletons of the blood vessels; and finding voxels within a predetermined spatial range from one of the extracted nodes, which is selected as the region of interest.

(12) The method for quantifying blood vessels, wherein the finding the voxels of blood vessels includes: generating offset surfaces defined as a set of voxels within a predetermined distance from the outer surface of the organ in an inward direction; and finding voxels corresponding to intersections between the extracted blood vessels and the offset surfaces.

(13) The method for quantifying blood vessels, wherein the quantifying the length information of the blood vessels includes: cylinder fitting the found voxels; and calculating the radii of the blood vessels at nodes using the cylinder fitted voxels.

(14) The method for quantifying blood vessels, wherein the quantifying the length information of the blood vessels includes: calculating offset areas that are formed by the voxels, corresponding to the intersections, on the offset surfaces; and calculating the radii of the blood vessels in a direction orthogonal to the vascular orientation vectors of the blood vessels using the surface normal vectors of the offset surfaces, the vascular orientation vectors of the blood vessels, and the offset areas.

(15) The method for quantifying blood vessels, wherein the extracting blood vessels includes: acquiring images of lungs; generating an initial pulmonary vessel tree by applying a minimum spanning tree method to pulmonary vessels included in the images of lungs; automatically separating the initial pulmonary vessel tree into sub-trees by eliminating a mediastinal region, in which pulmonary vessels aggregated, from the initial pulmonary vessel tree; remerging the sub-trees by extending the sub-trees to the mediastinal region of the initial tree from which the pulmonary vessels have been eliminated; and generating classified pulmonary vessel trees by classifying the pulmonary vessels of the remerged initial tree into pulmonary arteries and pulmonary veins.

(16) The method for quantifying blood vessels, wherein the finding the voxels of the blood vessels includes: generating a pulmonary artery skeleton and a pulmonary vein skeleton using the classified pulmonary vessel trees; extracting nodes, at which pulmonary vessel branches branch off, based on the pulmonary artery skeleton and the pulmonary vein skeleton; and finding neighbor boundary voxels at one of the extracted node, which is selected as the region of interest of the lungs; and wherein the quantifying the length information of the blood vessels includes: cylinder fitting the found voxels; and calculating the radii of the blood vessels at nodes using the cylinder fitted voxels.

(17) The method for quantifying blood vessels, wherein the finding the voxels of the blood vessels includes: generating offset surfaces defined as a set of voxels within a predetermined distance from an outer surface of the lungs in an inward direction; and finding voxels corresponding to intersections between the classified pulmonary vessel trees and the offset surfaces; and wherein the quantifying the length information of the blood vessels includes: calculating offset areas that are formed by the voxels, corresponding to the intersections, on the offset surfaces; and calculating the radii of the blood vessels in a direction orthogonal to the vascular orientation vectors of the blood vessels using the surface normal vectors of the offset surfaces, the vascular orientation vectors of the blood vessels, and the offset areas.

(18) The method for quantifying blood vessels, wherein the extracting nodes includes assigning ordered pairs to the nodes from an outer distal end of the lungs; and the finding voxels includes selecting nodes in the region of interest using the ordered pairs.

(19) The method for quantifying blood vessels, wherein the finding voxels corresponding to intersections includes: extracting the medial lines of the pulmonary vessels as the skeletons of the classified pulmonary vessel trees; extracting intersections between the medial lines and the offset surfaces; and finding neighbor boundary voxels at the intersections.

(20) The method for quantifying blood vessels, wherein the generating offset surfaces includes: separating the right lung and the left lung from the images of lungs as sets of voxels; generating Euclidean distance fields from the boundaries of the separated right and left lungs; and extracting iso-surfaces at a required offset distance.

(21) A computer-readable storage medium having stored thereon a computer program that, when executed by a computer, causes the computer to execute the method for quantifying blood vessels.

In accordance with a method for distinguishing between a pulmonary artery an a pulmonary vein according to the present disclosure, pulmonary arteries and pulmonary veins can be viewed in the state of being distinguished from each other.

Furthermore, in accordance with another method for distinguishing between a pulmonary artery an a pulmonary vein according to the present disclosure, pulmonary arteries and pulmonary veins can be viewed in the state of being distinguished from each other also in non-contrast medical images, such as CT scan images.

In accordance with a method for quantifying blood vessels according to the present disclosure, there is provided a quantification method for analyzing various characteristics representative of the distributions and scales of pulmonary arteries and pulmonary veins, i.e., the morphological characteristics of pulmonary vessels, such as average radii, the cross-sectional area of pulmonary vessels that intersect inner surfaces, and the area percentage of blood vessels in an overall pulmonary surface.

In accordance with a method for quantifying blood vessels according to the present disclosure, many lung diseases, such as pulmonary hypertension, interstitial lung disease and chronic obstructive pulmonary disease (COPD), can be more effectively evaluated based on a quantitative approach that takes into account the spatial distributions and scales of automatically classified small pulmonary arteries and pulmonary veins.

While the present invention has been described in conjunction with specific details, such as specific elements, and limited embodiments and diagrams above, these are provided merely to help an overall understanding of the present invention. The present invention is not limited to these embodiments, and various modifications and variations can be made based on the foregoing description by those having ordinary knowledge in the art to which the present invention pertains.

Accordingly, the technical spirit of the present invention should not be determined based on only the described embodiments, and the following claims, all equivalents to the claims and equivalent modifications should be construed as falling within the scope of the spirit of the present invention.

What is claimed is:

1. A method for quantifying blood vessels, comprising:
   extracting blood vessels as a three-dimensional (3D) set of voxels based on medical images of an organ;
   finding voxels of the blood vessels included in a region of interest of the organ; and
   quantifying length information of the blood vessels, including diameters of the blood vessels, by using the found voxels, and
   wherein the finding voxels of the blood vessels comprises:
   determining levels of the blood vessels based on morphological characteristics of the blood vessels or locations of the blood vessels in the organ, wherein the region of interest is selected based on the levels of the blood vessels.

2. The method of claim 1, wherein the quantifying length information of the blood vessels comprises:
   calculating radii of the blood vessels using the found voxels; and
   calculating an area ratio of the blood vessels to the region of interest using the calculated radii of the blood vessels.

3. The method of claim 1, wherein the finding voxels of blood vessels comprises:
   extracting medial lines of the extracted blood vessels;
   finding voxels along medial lines included in the region of interest; and
   finding neighbor boundary voxels from the voxels along the medial lines.

4. The method of claim 1, wherein the finding voxels of blood vessels comprises:
   generating skeletons of the blood vessels by extracting medial lines of the blood vessels;
   extracting nodes, at which blood vessels branch off, using the skeletons of the blood vessels; and
   finding voxels within a predetermined spatial range from one of the extracted nodes, which is selected as the region of interest.

5. The method of claim 1, wherein the finding voxels of blood vessels comprises:
   generating offset surfaces defined as a set of voxels within a predetermined distance from an outer surface of the organ in an inward direction; and
   finding voxels corresponding to intersections between the extracted blood vessels and the offset surfaces.

6. The method of claim 4, wherein the quantifying length information of the blood vessels comprises:
   cylinder fitting the found voxels; and
   calculating radii of the blood vessels at nodes using the cylinder fitted voxels.

7. The method of claim 5, wherein the quantifying length information of the blood vessels comprises:
   calculating offset areas that are formed by the voxels, corresponding to the intersections, on the offset surfaces; and
   calculating radii of the blood vessels in a direction orthogonal to vascular orientation vectors of the blood vessels using surface normal vectors of the offset surfaces, the vascular orientation vectors of the blood vessels, and the offset areas.

8. The method of claim 1, wherein the extracting blood vessels comprises:
   acquiring images of lungs;
   generating an initial pulmonary vessel tree by applying a minimum spanning tree method to pulmonary vessels included in the images of lungs;
   automatically separating the initial pulmonary vessel tree into sub-trees by eliminating a mediastinal region, in which pulmonary vessels aggregated, from the initial pulmonary vessel tree;
   remerging the sub-trees by extending the sub-trees to the mediastinal region of the initial tree from which the pulmonary vessels have been eliminated; and
   generating classified pulmonary vessel trees by classifying pulmonary vessels of the remerged initial tree into pulmonary arteries and pulmonary veins.

9. The method of claim 8, wherein:
   the finding voxels of the blood vessels comprises:
   generating a pulmonary artery skeleton and a pulmonary vein skeleton using the classified pulmonary vessel trees;
   extracting nodes, at which pulmonary vessel branches branch off, based on the pulmonary artery skeleton and the pulmonary vein skeleton; and
   finding neighbor boundary voxels at one of the extracted node, which is selected as the region of interest of the lungs; and
   the quantifying length information of the blood vessels comprises:
   cylinder fitting the found voxels; and
   calculating radii of the blood vessels at nodes using the cylinder fitted voxels.

10. The method of claim 8, wherein:
    the finding voxels of the blood vessels comprises:
    generating offset surfaces defined as a set of voxels within a predetermined distance from an outer surface of the lungs in an inward direction; and
    finding voxels corresponding to intersections between the classified pulmonary vessel trees and the offset surfaces; and
    the quantifying length information of the blood vessels comprises:
    calculating offset areas that are formed by the voxels, corresponding to the intersections, on the offset surfaces; and
    calculating radii of the blood vessels in a direction orthogonal to vascular orientation vectors of the blood vessels using surface normal vectors of the offset surfaces, the vascular orientation vectors of the blood vessels, and the offset areas.

11. The method of claim 9, wherein:
    the extracting nodes comprises:
    assigning ordered pairs to the nodes from an outer distal end of the lungs; and
    the finding voxels comprises:
    selecting nodes in the region of interest using the ordered pairs.

12. The method of claim 10, wherein the finding voxels corresponding to intersections comprises:
    extracting medial lines of the pulmonary vessels as skeletons of the classified pulmonary vessel trees;
    extracting intersections between the medial lines and the offset surfaces; and
    finding neighbor boundary voxels at the intersections.

13. The method of claim 10, wherein the generating offset surfaces comprises:

separating a right lung and a left lung from the images of lungs as sets of voxels;

generating Euclidean distance fields from boundaries of the separated right and left lungs; and extracting iso-surfaces at a required offset distance.

14. A non-transitory computer-readable medium containing program instructions that, when executed by a processor, causes the processor to execute a method of quantifying blood vessels, comprising:

program instructions that extract blood vessels as a three-dimensional (3D) set of voxels based on medical images of an organ;

program instructions that find voxels of the blood vessels included in a region of interest of the organ; and program instructions that quantify length information of the blood vessels, including diameters of the blood vessels, by using the found voxels, and wherein the program instructions that find voxels of the blood vessels comprises:

program instructions that determine levels of the blood vessels based on morphological characteristics of the blood vessels or locations of the blood vessels in the organ, wherein the region of interest is selected based on the levels of the blood vessels.

* * * * *